United States Patent
Steffen (10) Patent No.: US 8,684,282 B2
(45) Date of Patent: Apr. 1, 2014

(54) ADJUSTABLE SPRAY PATTERN ATOMIZER

(75) Inventor: Dennis L. Steffen, Tavernier, FL (US)

(73) Assignee: Plantation Key Design Inc., Tavernier, FL (US)

( * ) Notice: Subject to any disclaimer, the term of this patent is extended or adjusted under 35 U.S.C. 154(b) by 253 days.

(21) Appl. No.: 12/258,076

(22) Filed: Oct. 24, 2008

(65) Prior Publication Data

US 2009/0108091 A1 Apr. 30, 2009

Related U.S. Application Data

(60) Provisional application No. 61/000,281, filed on Oct. 25, 2007.

(51) Int. Cl.
*A62C 5/02* (2006.01)

(52) U.S. Cl.
USPC ............ 239/8; 239/402.5; 239/422; 239/428; 239/490; 239/491; 239/493; 222/145.5; 222/145.8; 604/90

(58) Field of Classification Search
USPC .......... 239/402.5, 465, 472, 428, 422, 490, 8, 239/432, 491, 493; 604/82, 90; 222/145.5, 222/145.8
See application file for complete search history.

(56) References Cited

U.S. PATENT DOCUMENTS

| | | | | |
|---|---|---|---|---|
| 1,629,288 | A * | 5/1927 | Morse | 239/402.5 |
| 2,697,638 | A | 12/1954 | Anger | |
| 2,991,015 | A * | 7/1961 | Standlick | 239/127 |
| 3,054,563 | A * | 9/1962 | Steinen | 239/492 |
| 3,100,084 | A * | 8/1963 | Biber | 239/463 |
| 3,102,691 | A | 9/1963 | Gall | |
| 3,417,923 | A * | 12/1968 | Carlson | 239/112 |
| 4,013,228 | A * | 3/1977 | Schneider | 239/401 |
| 4,631,055 | A * | 12/1986 | Redl et al. | 604/82 |
| 4,991,778 | A * | 2/1991 | Maas et al. | 239/333 |
| 2,343,647 | A | 3/1994 | Doerr | |
| 5,388,768 | A * | 2/1995 | Moses | 239/417.5 |
| 5,641,125 | A * | 6/1997 | Martin et al. | 239/481 |
| 6,733,472 | B1 * | 5/2004 | Epstein et al. | 604/30 |
| 2003/0192964 | A1 | 10/2003 | Foster et al. | |
| 2003/0209612 | A1 * | 11/2003 | Hahnen | 239/398 |
| 2007/0164459 | A1 | 7/2007 | Gottlieb et al. | |

OTHER PUBLICATIONS

International Search Report and Written Opinion for Application No. PCT/US2008/081163 dated Dec. 24, 2008 (9 pages).

* cited by examiner

*Primary Examiner* — Dinh Q Nguyen
(74) *Attorney, Agent, or Firm* — Michael Best & Friedrich LLP

(57) ABSTRACT

An atomizer delivery manifold or spray head with an adjustable spray pattern tip is provided. The adjustable spray pattern atomizer is especially useful for delivery of fibrin glues, and enables a fluid admixture to be applied precisely to a specific site in a wide range of spray patterns.

15 Claims, 6 Drawing Sheets

ADJUSTABLE SPRAY PATTERN ATOMIZER

CROSS REFERENCES TO RELATED APPLICATIONS

This application claims the benefit under 35 U.S.C. §119(e) of U.S. Provisional Application No. 61/000,281 filed on Oct. 25, 2007, the complete disclosure of which is incorporated herein by reference in its entirety.

FIELD OF THE INVENTION

The invention relates to an atomizer delivery system and method for the application of fibrin glues.

INTRODUCTION

Specialized devices are used for dispensing a plurality of different, i.e., separate, fluid medications or agents as an admixed product. For example, specialized spray heads are used for delivering two biochemically reactive fluids, such as fibrinogen and thrombin to form fibrin in an admixed state, to a biological surface. The biochemically reactive fluids may be delivered topically, in open-type surgeries such as laparotomic procedures, and in minimally invasive surgeries such as laparoscopic procedures.

There exist many techniques for the application of fibrin glues or sealants. In one method, the fibrin sealant components are drawn into a syringe and ejected via an appropriate sized needle. In another method, a double barrel syringe is used. Other conventional techniques include a microdrop delivery system, and a spray application via a multi-channel catheter, which is fixed, to a pressurized air/gas source. These conventional atomizers work by delivering the fibrin glue in a fixed non-adjustable spray pattern.

BRIEF DESCRIPTION

An atomizer delivery manifold or spray head with an adjustable spray pattern tip is provided in accordance with the principles embodying the invention. The adjustable spray pattern atomizer in accordance with the invention is especially useful for delivery of fibrin glues, and enables a fluid admixture to be applied precisely to a specific site in a wide range of spray patterns. The tip is matedly engaged with and in fluid communication with a distal end of the manifold, and has an aperture through which fluids are dispensed. The tip is adjustable by movement and positioning of the tip with respect to the manifold. Such movement and positioning varies the fluid pressure at the tip. As the tip is tightened onto the manifold, the pressure increases, and the spray pattern widens. As tip is loosened, the pressure decreases, and the spray pattern narrows.

In one embodiment, the spray head tip is suitably adjustable by rotating the tip in a clockwise or counter clockwise direction on to the manifold. In another embodiment, an adjustable spray pattern is suitably provided by moving the tip in a back and forth linear or reciprocating manner direction with respect to the manifold. The aperture of the tip may be varied in size by utilizing a tip with a different aperture size. This may suitably affect the particulate size of the substance being atomized, e.g., a smaller aperture would result in a smaller particulate size.

Although the invention is particularly suitable for application of fibrin glues and described as such in an illustrated embodiment, it should not be construed as limited only to such application.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

A delivery atomizer system, especially a fibrin glue atomizer system, embodying the principles of the invention is provided. The system includes a manifold or spray head and a specialized spray tip.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "mounted," "connected," "supported," and "coupled" and variations thereof herein are used broadly and encompass both direct and indirect mountings, connections, supports, and couplings. Further, "connected" and "coupled" are not restricted to physical or mechanical connections or couplings.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

In view of the foregoing disadvantages inherent in conventional fibrin glue application systems, the invention provides a novel system and method for application of fluid components, especially fibrin glues. Given that many fibrin glue delivery systems are capable of only one fixed spray pattern and particulate size, it has been found advantageous to have a variable spray pattern, allowing greater precision in the area of application. In an illustrated embodiment, the invention provides an adjustable spray pattern for fibrin glue delivery in the form of an spray tip having unlimited adjustments and capable of producing myriad spray effects. The full advantage of the adjustable spray tip in accordance with the invention is realized when optimal spray area is achieved for a particular biological surface, thus allowing for the fibrin glue solution to be applied as effectively as possible.

As noted, the invention is illustrated with reference to fibrin glue or sealants. Fibrin sealants are formed from blood plasma components and typically comprise a first agent containing fibrinogen and Factor XIII and a second agent which usually includes a fibrinogen activator such as thrombin and calcium ions, the two agents being mixed together just prior to use. Fibrin sealants, in effect, mimic the last step of the natural coagulation cascade and are usually commercialized as kits comprising the two main agents. After mixing of the agents, the fibrinogen is proteolytically cleaved by thrombin, and converted into fibrin monomers. Factor XIII is also cleaved by thrombin into its activated form which crosslinks the fibrin monomers to form a three-dimensional network that acts as a tissue adhesive or biological adhesive or bioadhesive, and is commonly known as a fibrin clot or fibrin glue. The reaction is rapid and typically commences within a few seconds after the components initially contact one another and attains a soft set after several more seconds of contact.

Features of the system in accordance with the invention to delivering fibrin glue to a biological surface are advantageous. For example, during the surgical act of applying the fibrin glue to the desired area, other soft tissue may be in the way of the path of the intended application zone. In accordance with the invention, a surgeon is able to avoid undue contact with soft tissue or even minimize soft tissue dissection by choosing the more suitable spray pattern afforded by the adjustment of the tip. Therefore, an additional benefit of the adjustable spray pattern design is its versatility, minimizing the requirement for soft tissue dissection and retraction.

In one embodiment, the invention provides an atomizer delivery manifold or spray head suitable for attachment to, and use with, a supply device for application of a mixture of two or more separate fluid components to a surface in varying spray patterns. In general, the manifold or spray head suitably includes two or more branched portions and a common portion or mixing chamber. Each branched portion has an entry port for receiving a fluid component and an exit port into the common portion. The entry ports are attachable to the supply device for dispensing each of the separate components into the branched channels. The common portion or mixing chamber is for receiving and mixing the components to form a mixture and has a common portion exit port. The manifold or spray head also includes a gas channel for carrying gas into the common portion for atomizing and propelling the mixture through the common portion exit port. In accordance with the invention, the manifold or spray head includes an adjustable spray tip having an aperture through which the fluid admixture emanates. The spray tip is in fluid communication with the manifold or spray head and is capable of movement with respect to same. The spray tip can be tightened with respect to the manifold. In doing so, the fluid pressure at the tip is increased, and the spray pattern widens. The spray tip can be loosened. In doing so, the fluid pressure is decreased, and the spray pattern narrows.

In another aspect, the invention is a system for mixing and delivering two or more fluids as an admixed composition in an atomized spray and capable of variable spray patterns, the fluids being admixed just prior to spray application to a surface. In an illustrated embodiment, the system includes a syringe assembly and a discharge manifold assembly or spray head. The manifold assembly or spray head includes a spray tip that is in a mated relationship with and capable of movement and positioning with respect to the manifold body, i.e., the tip can be tightened or loosened to the manifold. The syringe assembly includes syringes for holding and dispensing each fluid. The discharge manifold assembly or spray head is for receiving fluid from each syringe, for mixing the fluids from both syringes and for delivering the mixed composition in a spray through the aperture of the spray tip with an adjustable spread pattern. The discharge manifold or spray head is coupled to the exit ports of the syringe assembly. The discharge manifold assembly includes channels therethrough communicating with exit ports from the syringe assembly, for carrying each fluid in its corresponding channel within the manifold. The spray head or discharge manifold also includes a mixing chamber having an exit opening, to receive and mix the separate flows from the channels; and a gas line having an exit port, for carrying a pressurized gas to the mixing chamber. The fluids are mixed in the mixing chamber to form a mixed composition or admixture that is immediately entrained by the gas, and atomized and discharged in a spray through the spray tip that capable of providing varying spray pattern. The movement and positioning of the tip with respect to the manifold, i.e., the tightening or loosening of the tip, varies the fluid pressure to the tip, and hence varies the spray pattern of fluids emanating from the tip. In one embodiment, movement of the tip is achieved by threadly attaching the tip to the manifold and rotating the tip. In another embodiment, movement of the tip is achieved by the tip being a linear sleeve capable of back and forth motion to tighten or loosen the tip. Each embodiment includes an external manipulating member to facilitate movement and positioning of the tip.

Reference is now made to FIGS. 1-6 wherein a delivery manifold or spray head in accordance with the invention is depicted and generally designated by reference numeral 10. Spray head 10 is removably attached or connected to a fluid delivery device, having separate fluid delivery containers/vessels.

Figure 1:
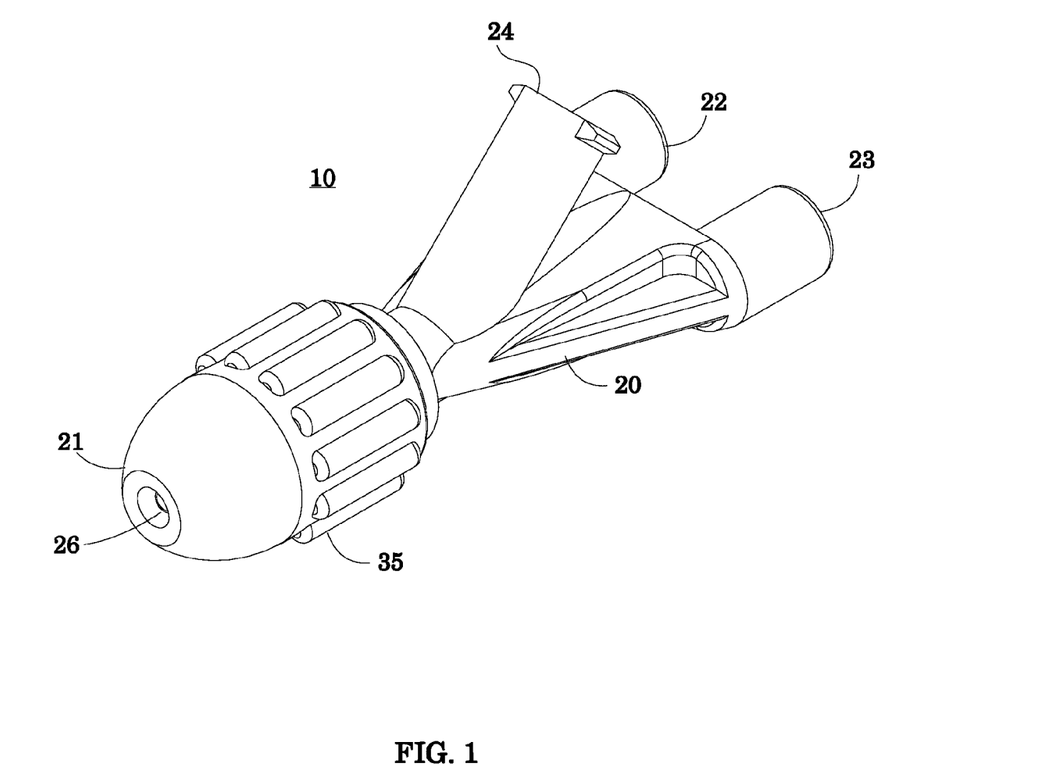
FIG. 1 is an isometric view of the rotating tip configuration of the atomizer manifold, all in accordance with the invention.
Figure 2:
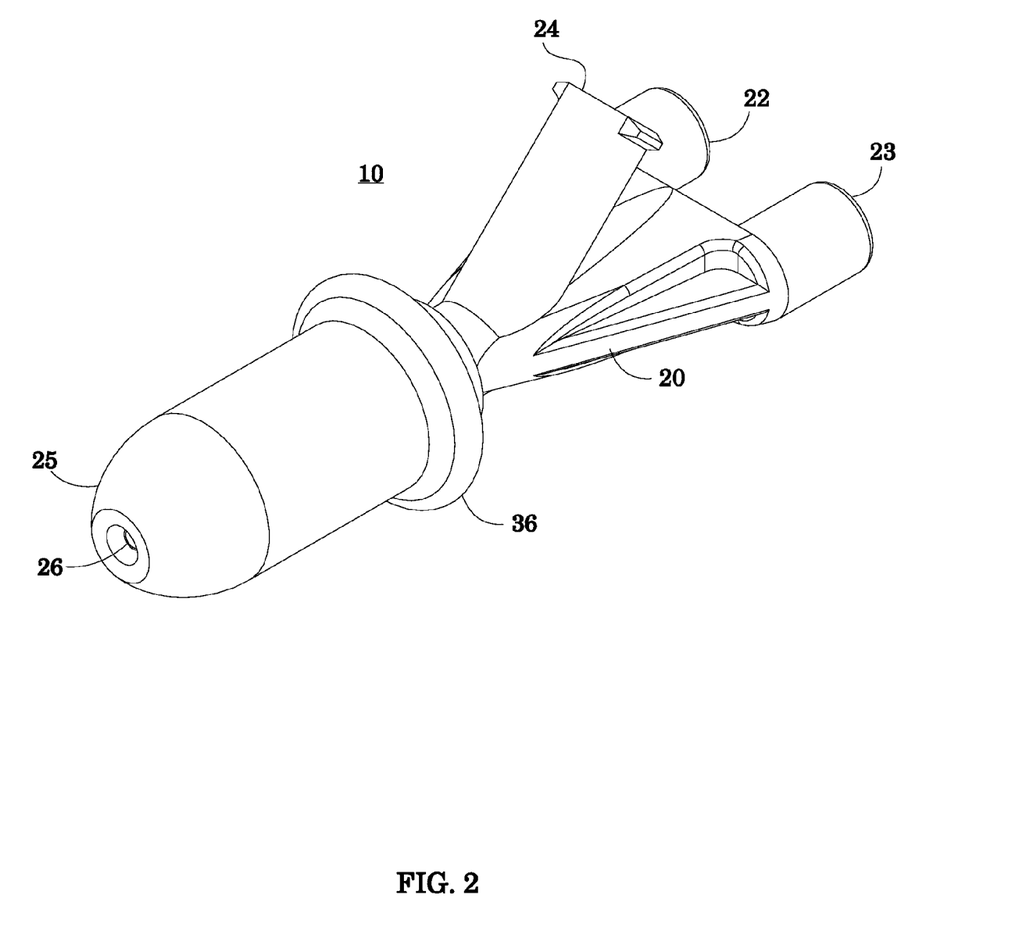
FIG. 2 is an isometric view of the linear movement tip configuration of the atomizer manifold, all in accordance with the invention.

System 10 includes a manifold 20 and a rotating spray tip 21 or a linear tip 25 for delivery of fibrin glues. In an illustrated embodiment, manifold 20 is defined by a first solution channel 22 and a second solution channel 23 which are opposed to the third air/gas channel 24. Manifold 20 connects to two solution sources, e.g., syringes, and one air/gas source e.g., low pressure compressed air. Manifold 20 can optionally be configured in this manner but not limited to this configuration.

The manifold 20 includes a configuration for the mating of a spray tip. The mating configuration on the manifold may consist of a threaded or linear shaft depending on the tip adjustment method.

As shown in FIG. 1, the rotating tip 21 adjusts the spray pattern by rotating the tip in a clockwise or counter clockwise direction. The tip has raised fluted features or projections 35 to aid in gripping. As the tip is rotated in a clockwise direction, the tip is tightened and the spray pattern angle widens. When turn in a counter clockwise direction, the tip is loosened and the spray pattern angle narrows.

It is also noted that depending on the size of tip aperture 26, the particulate size may be affected proportionately. Theoretically, as the tip is rotated clockwise, increasing the pressure at which the fluid is forced through the tip's aperture, the particulate size would become finer. Similarly as the tip is rotated counter clockwise, thus lessening restriction and reducing pressure, the particulate size would become larger. The aperture size may be defined per individual tip configuration e.g. a tip with a larger aperture would produce a larger particulate size and a tip configuration with a smaller aperture would produce a smaller particulate size. Spray tips with varying apertures may be provided as a kit, the tips being selected according to application required.

As shown in FIG. 2, the linear tip 25 adjusts the spray pattern by sliding the tip in a reciprocating fashion, i.e., a back and forth direction. As the tip is slide in the direction of the manifold 20, the spray pattern angle widens. When the tip is slide in the direction away from the manifold 20, the spray pattern angle narrows. The flanged area 36 on the proximal end of the tip provides a grip area during movement. Specifically, as the tip is slid in the direction of the manifold, restricting therefore and increasing the pressure at which the fluid is forced through the tip's aperture, the spray pattern angle widens. Similarly, as the tip is slide in the direction away from the manifold, thus lessening restriction and reducing pressure, the spray pattern angle narrows.

Figure 3:
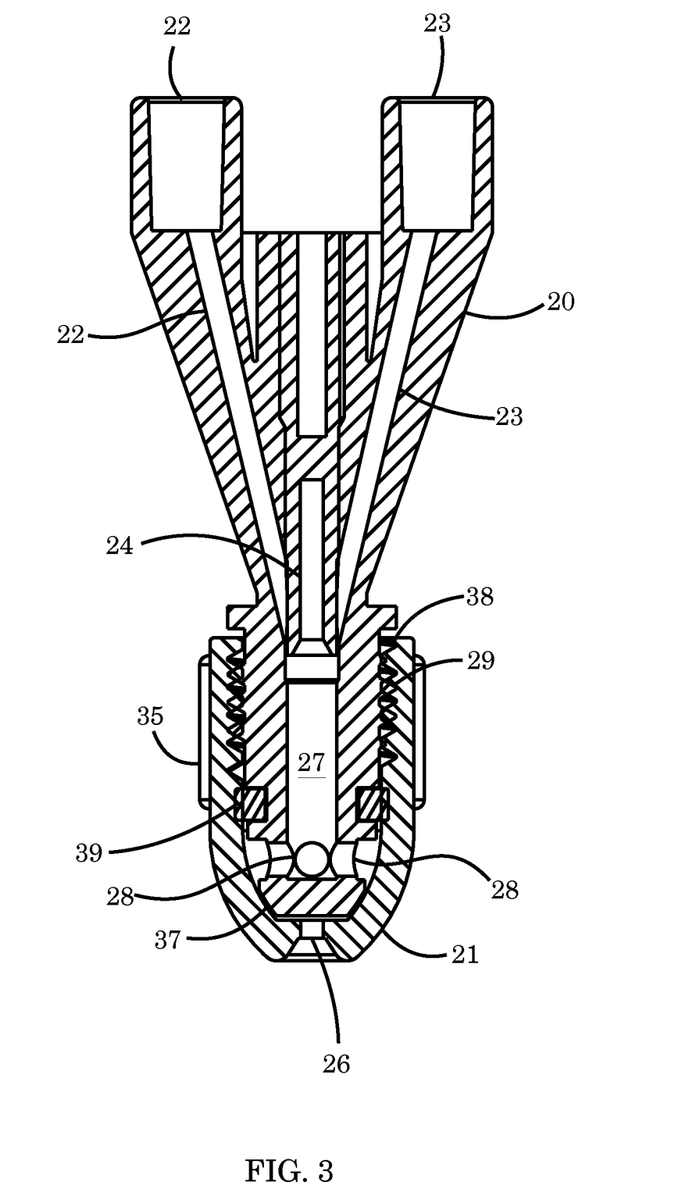
FIG. 3 is a cross section view of the solution channels configuration of the atomizer manifold, all in accordance with the invention.

Cross-sectional views of the interior of system 10 are illustrated in FIG. 3. The interior of spray head 10 includes a mixing chamber 27, air/gas channel 24, and component or solution conduits or channels 22 and 23 that suitably have syringe-connecting or inlet ports, and mixing-chamber connecting or exit ports. The channels 22 are aligned with syringe exit openings or ports of the syringe tips. Channels 22 and 23 lead from the syringe tips to and end at mixing chamber 27 which is proximate aperture 26. In an illustrated embodiment, channels 22 and 23 are suitably disposed at an acute angle to each other (although larger angles are suitably contemplated) and converge at the mixing chamber 27. In other words, in the illustrated embodiment, the internal or interior channels of head 10 form, in effect, a branched configuration in which the branches are the channels 22 and 23 and the base or leg is the mixing chamber 27. Conduits 22 and 23 provide fluid communication between the syringes and the mixing chamber. As is seen in FIG. 3, channels/conduits 22, 23 and 24 are unvalved.

As the solutions are combined in mixing chamber 27 and the pressure from the air/gas source is applied, the mixture is forced out though the manifold and then through aperture 26 in the tip. As shown in FIG. 3, the movement of the tip is controlled by a thread 38 on the tip which mates with a thread 29 on the manifold. The manifold has a curved shape on the most distal end 37 which matches the shape of the interior surface of the tip 21. An O-ring 39 can be an individual component or molded into the manifold. O-ring 39 provides a seal between tip 21 and manifold 20.

Figure 4:
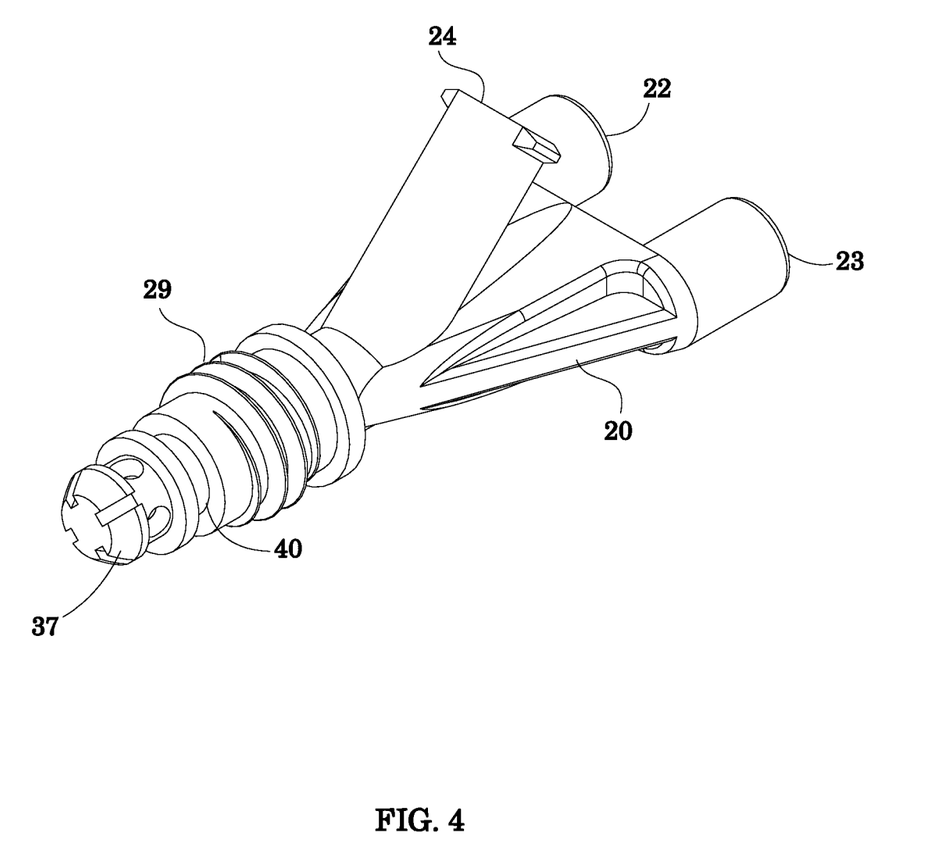
FIG. 4 is an isometric view of the atomizer manifold with the rotating tip removed to display the thread configuration used in indexing of the tip, all in accordance with the invention.

As shown in FIG. 4, the external threaded portion 29 of manifold 20 which corresponds with a mating internal thread 38 on the rotating tip 21 is used in rotating tip. The thread is typically right hand in direction. The distal end 37 of the manifold also provides an O-ring groove 40 when required.

Figure 5:
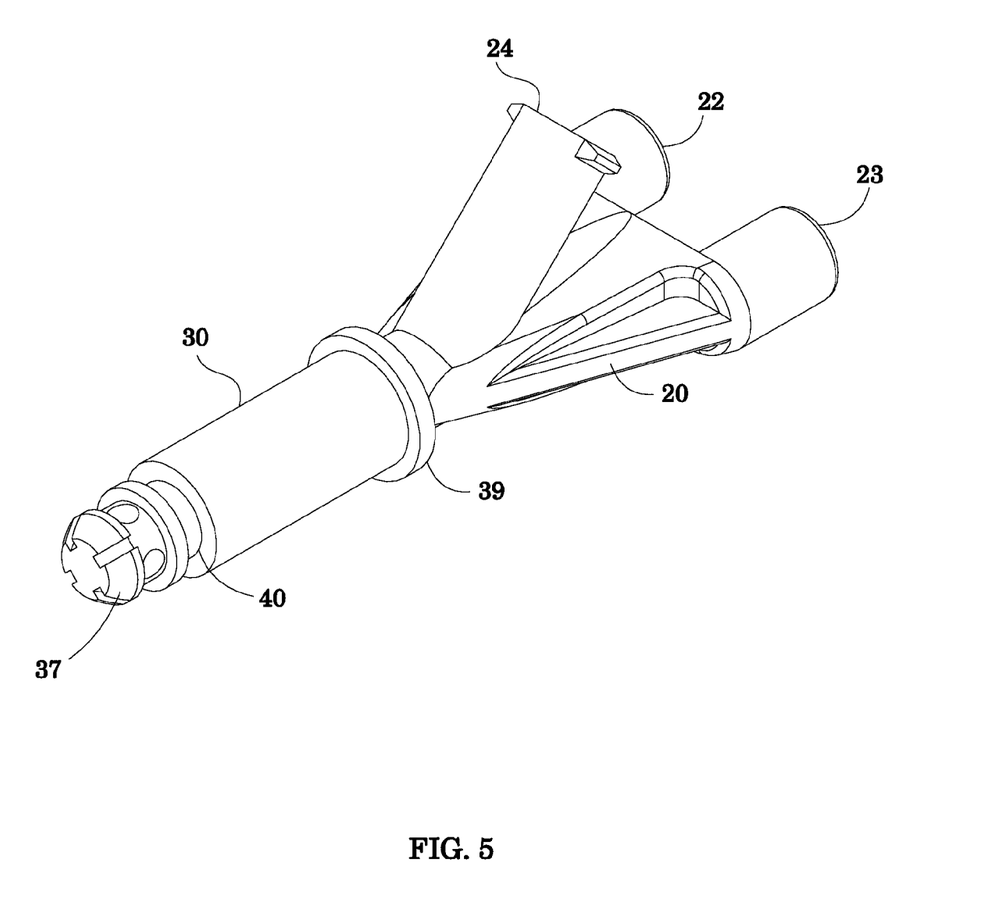
FIG. 5 is an isometric view of the atomizer manifold with the linear tip removed to display the shaft configuration used in indexing of the tip, all in accordance with the invention.

As shown in FIG. 5, a shaft portion 30 of manifold 20 corresponds with a mated orifice on the linear tip 25. Tip 25 slides on shaft 30, allowing movement of the linear tip. A rear flange 39 on the proximal provides a physical stop for the linear tip.

Figure 6:
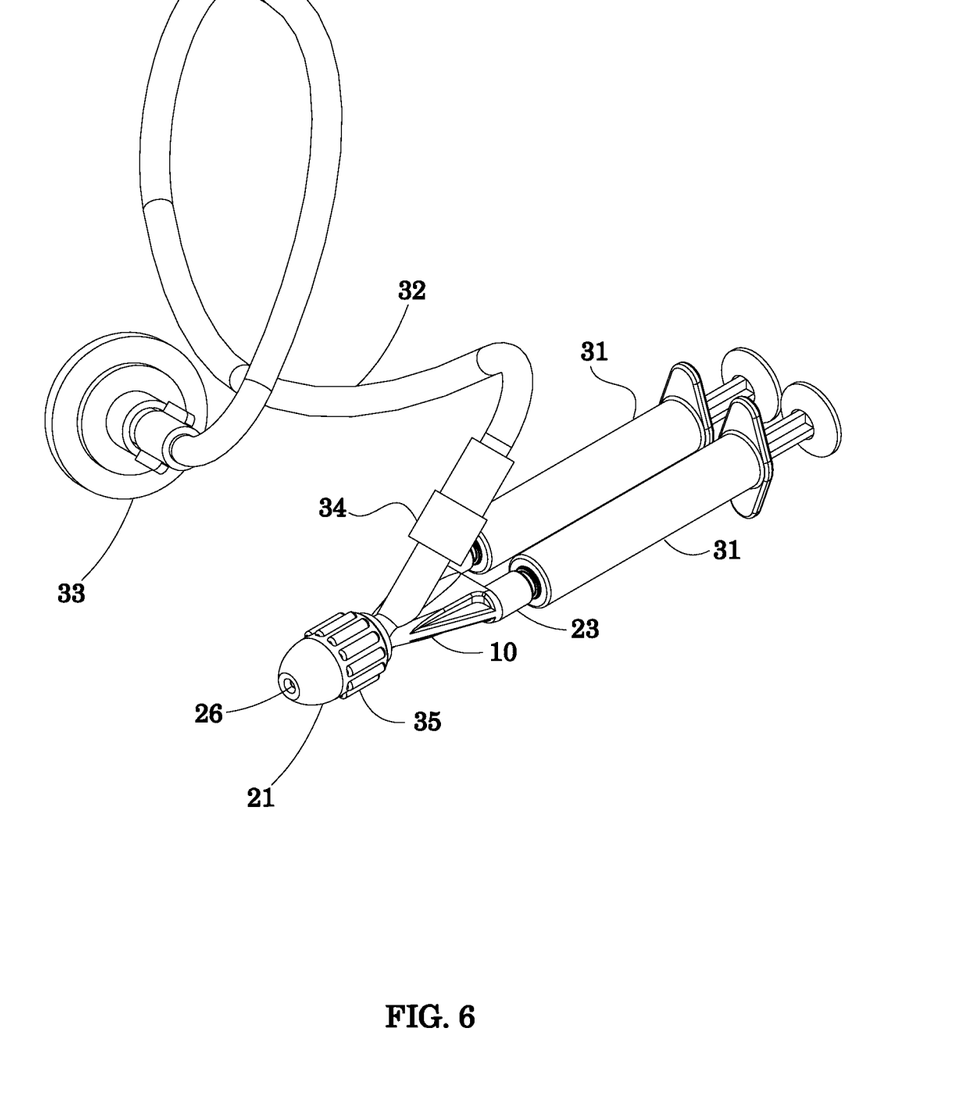
FIG. 6 is an isometric view of the atomizer manifold attached to a dual syringe solution delivery system and air/gas source, all in accordance with the invention.

In an illustrated embodiment shown in FIG. 6, delivery device is suitably a dual syringe assembly having syringes 31. Syringes 31 of the assembly contain and hold the fluid components to be mixed and are suitably arranged in a parallel fashion. Typically, the syringes are commonly held and can be actuated by common means. In providing a fibrin adhesive/sealant as a mixed product, one syringe contains a fibrinogen component/solution and the other a solution of fibrinogen activator such as thrombin. Other containers (e.g., fluid containers other than syringes, more than one container, etc.) are also possible for use with manifold or spray head 10. The rotating tip 21 embodiment is illustrated in FIG. 6 with the solution syringes 31 and air/gas source 32 connected. The air/gas source is connected to the manifold with a luer fitting 34 and connected to the air/gas source origin with an in-line filter 33 connection.

In operation of the illustrated embodiment, the syringes are filled with the component solutions to be mixed. In the case of a fibrin sealant, one syringe suitably contains a fibrinogen solution and the other a thrombin solution. Pressure is applied to the plungers of the syringes, causing the solutions in the syringes to flow into the channels of the manifold. The two solutions flow through their respective channels to meet in mixing chamber 27 where the solutions are mixed to form an admixed product or composition. The two solutions suitably enter the mixing chamber 27 in separate streams at angle to each other, facilitating mixing the solutions. Gas flow is released via the gas connector into mixing chamber 27, mixing with the mixed composition. The mixed composition in the gas flow is entrained and atomized and emerges from aperture 26. The spray pattern, depending on the target surface, can be tailored by the movement, i.e., tightening or loosening, of the tip, providing a focused spray pattern to the surface.

System 10 can be conveniently made of a one-piece or unitary construction. Materials for the system are not particularly limited but are suitably made of a common synthetic material used in the medical field, such as polyolefin (polyethylene, polypropylene), polyurethane, PVC, ACS (acrylonitrile butadiene styrene), or polyester, by injection molding or by extrusion. Channels 22 and 23 are suitably made of Teflon™, polymeric material, or the like.

The source of gas/air can be a line from a remote source or a cartridge attached to system 10 via a connector. The gas is typically actuated in a common manner with component actuation (e.g., syringe actuation) or may have independent gas actuation.

In summary, the present invention provides a system for delivery of a multi-component composition in which the components are mixed just prior to application and a spray of the admixed components is delivered onto a target, e.g., a biological surface. A unique adjustable spray tip capable of varying spray patterns provides advantages over known spray devices.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The invention claimed is:

1. An atomizer delivery manifold comprising:
an unvalved first solution channel;
an unvalved second solution channel;
an unvalved gas channel;
a mixing chamber in direct communication with the first solution channel, the second solution channel, and the gas channel; and
an adjustable spray pattern tip, the tip configured to be in direct mating relationship and in fluid communication with a distal end of the manifold, the manifold having a curved shape at the distal end which matches the inner surface of the tip, the tip having an aperture through which fluids are atomized, and an external manipulating portion having gripping projections or a flanged area to facilitate movement of the tip wherein the tip is tightened or loosened within the spray head assembly, and the fluid flow is restricted between the inner surface of the tip and the distal end of the manifold, and thereby varying the pattern of spray of the fluids through the spray tip.

2. The manifold of claim 1, wherein the spray tip is rotatable to adjust the spray angle of the spray.

3. The manifold of claim 2, wherein the spray tip is reciprocatable to adjust the spray angle of the spray.

4. The manifold of claim 3, wherein the tip has an external manipulating portion to facilitate movement and positioning of the tip.

5. The manifold of claim 3, wherein the spray tip includes a sleeve portion and the manipulating portion is a flange, grippable to facilitate back and forth motion of the tip.

6. The manifold of claim 1 wherein the unvalved first solution channel inlet and the unvalved second solution channel inlet are configured to accept a medical syringe fitting and the unvalved gas channel inlet is configured to accept a luer fitting.

7. An adjustable spray head tip for a spray head assembly, the tip configured to be in direct mating relationship and in fluid communication with a distal end of a manifold, the manifold having a curved shape at the distal end which matches the inner surface of the tip, the tip having an aperture through which fluids are atomized, and an external manipulating portion having gripping projections or a flanged area to facilitate movement of the tip wherein the tip is tightened or loosened within the spray head assembly, and the fluid flow is restricted between the inner surface of the tip and the distal end of the manifold, and thereby varying the pattern of spray of the fluids through the spray tip.

8. The spray tip of claim 7 further comprising a raised external manipulating portion which facilitates movement and positioning of the tip.

9. The spray tip of claim 8, wherein the external manipulating portion facilitates a rotation motion of the tip with respect to the spray head.

10. The spray tip of claim 8, wherein the external manipulating portion facilitates a back and forth movement of the tip with respect to the spray head.

11. A method of spraying fibrin glues, comprising:

delivering gas or air and components of the fibrin glue to a spray head having a first solution channel, a second solution channel, a gas channel, a mixing chamber, and a spray tip; the tip configured to be in direct mating relationship and in fluid communication with a distal end of a manifold, the manifold having a curved shape at the distal end which matches the inner surface of the tip, the tip having a discharge aperture through which fluids are atomized, and an external manipulating portion having gripping projections or a flanged area to facilitate movement of the tip wherein the tip is tightened or loosened within the spray head assembly, and the fluid flow is restricted between the inner surface of the tip and the distal end of the manifold, and thereby varying the pattern of spray of the fluids through the spray tip;

mixing the gas or air and the components in the mixing chamber to form an admixed product;

delivering the admixed product to the spray tip, varying the pattern of spray for the admixed product by moving and positioning the tip relative to the manifold; and discharging the admixed product through the aperture to a biological surface.

12. A spray atomizer system for delivering a fluid mixture in varying spray patterns, comprising:

a manifold having unvalved conduits for receiving fluids and a mixing chamber for receiving and mixing the fluids, an unvalved gas channel for receiving gas or air for mixing the fluids in the mixing chamber, and an adjustable spray pattern tip, the tip configured to be in direct mating relationship and in fluid communication with a distal end of the manifold, the manifold having a curved shape at the distal end which matches the inner surface of the tip, the tip having an aperture through which fluids are atomized, and an external manipulating portion having gripping projections or a flanged area to facilitate movement of the tip wherein the tip is tightened or loosened within the spray head assembly, and the fluid flow is restricted between the inner surface of the tip and the distal end of the manifold, and thereby varying the pattern of spray of the fluids through the spray tip.

13. The system of claim 12, wherein the tip is a linear member capable of reciprocating motion so as to move the tip with respect to the manifold.

14. A device for applying fibrin glues or sealants, comprising:

commonly actuable reservoirs for each component of a fibrin sealant, a source of gas, a manifold having unvalved conduits for receiving fluids and a mixing chamber for receiving and mixing the components and gas to form a sealant mixture, and an adjustable spray pattern tip, the tip configured to be in direct mating relationship and in fluid communication with a distal end of the manifold, the manifold having a curved shape at the distal end which matches the inner surface of the tip, the tip having an aperture through which fluids are atomized, and an external manipulating portion having gripping projections or a flanged area to facilitate movement of the tip wherein the tip is tightened or loosened within the spray head assembly, and the fluid flow is restricted between the inner surface of the tip and the distal end of the manifold, and thereby varying the pattern of spray of the fluids through the spray tip.

15. A method of delivering components of fibrin glues, comprising:

delivering gas or air and components of the fibrin glue to a spray head having a first solution channel, a second solution channel, a gas channel, a mixing chamber, and an adjustable spray pattern tip; the tip configured to be in direct mating relationship and in fluid communication with a distal end of a manifold, the manifold having a curved shape at the distal end which matches the inner surface of the tip, the tip having a discharge aperture through which fluids are atomized, and an external manipulating portion having gripping projections or a flanged area to facilitate movement of the tip wherein the tip is tightened or loosened within the spray head assembly, and the fluid flow is restricted between the inner surface of the tip and the distal end of the manifold, and thereby varying the pattern of spray of the fluids through the spray tip;

mixing the gas or air and the components in the mixing chamber to form an admixed product;

delivering the admixed product to the adjustable spray pattern tip;

varying the spray pattern angle for the admixed product emanating from the adjustable spray pattern tip by moving and positioning the adjustable spray pattern tip relative to the manifold; and discharging the admixed product through the aperture to a biological surface.

* * * * *